United States Patent [19]

Pagani

[11] Patent Number: 5,573,734
[45] Date of Patent: Nov. 12, 1996

[54] PLANT FOR THE PRODUCTION OF UREA IN REACTION SPACES WITH DIFFERENT YIELDS

[75] Inventor: Giorgio Pagani, Milan, Italy

[73] Assignee: Urea Casale S.A., Lugano-Besso, Switzerland

[21] Appl. No.: 462,635

[22] Filed: Jun. 5, 1995

Related U.S. Application Data

[63] Continuation of Ser. No. 236,574, May 2, 1994, Pat. No. 5,523,482.

[30] Foreign Application Priority Data

May 14, 1993 [CH] Switzerland ............... 01-471/93

[51] Int. Cl.⁶ ............................................. C07C 273/04
[52] U.S. Cl. ............................................. 422/189; 422/187
[58] Field of Search ............................. 422/189, 187; 564/67

[56] References Cited

U.S. PATENT DOCUMENTS

| | | |
|---|---|---|
| 3,005,849 | 10/1961 | Otsuka. |
| 4,801,745 | 1/1989 | Meessen et al.. |
| 5,380,943 | 1/1995 | Pagani et al. ............... 564/67 |

FOREIGN PATENT DOCUMENTS

| | | |
|---|---|---|
| 0479103 | 4/1992 | European Pat. Off.. |
| 0497215 | 8/1992 | European Pat. Off.. |

*Primary Examiner*—Timothy McMahon
*Attorney, Agent, or Firm*—Sughrue, Mion, Zinn, Macpeak & Seas

[57] ABSTRACT

In a process of producing urea in which ammonia and carbon dioxide are reacted in a first reaction space (E-1, R-1) the unreacted carbamate present in the reaction mixture is subjected to a thermal decomposition treatment, so as to obtain ammonia and carbon dioxide which are sent to a second reaction space (R-2) in which they react with a solution of recycled carbamate coming from an urea recovery section (3). Advantageously, the regulation of the temperature and of the ammonia/carbon dioxide molar ratio in the second reaction space (R-2) is carried out by respectively regulating the temperature of the recycled carbamate solution and the temperature of the thermal decomposition treatment of the residual carbamate leaving the first reaction space (E-1, R-1).

5 Claims, 1 Drawing Sheet

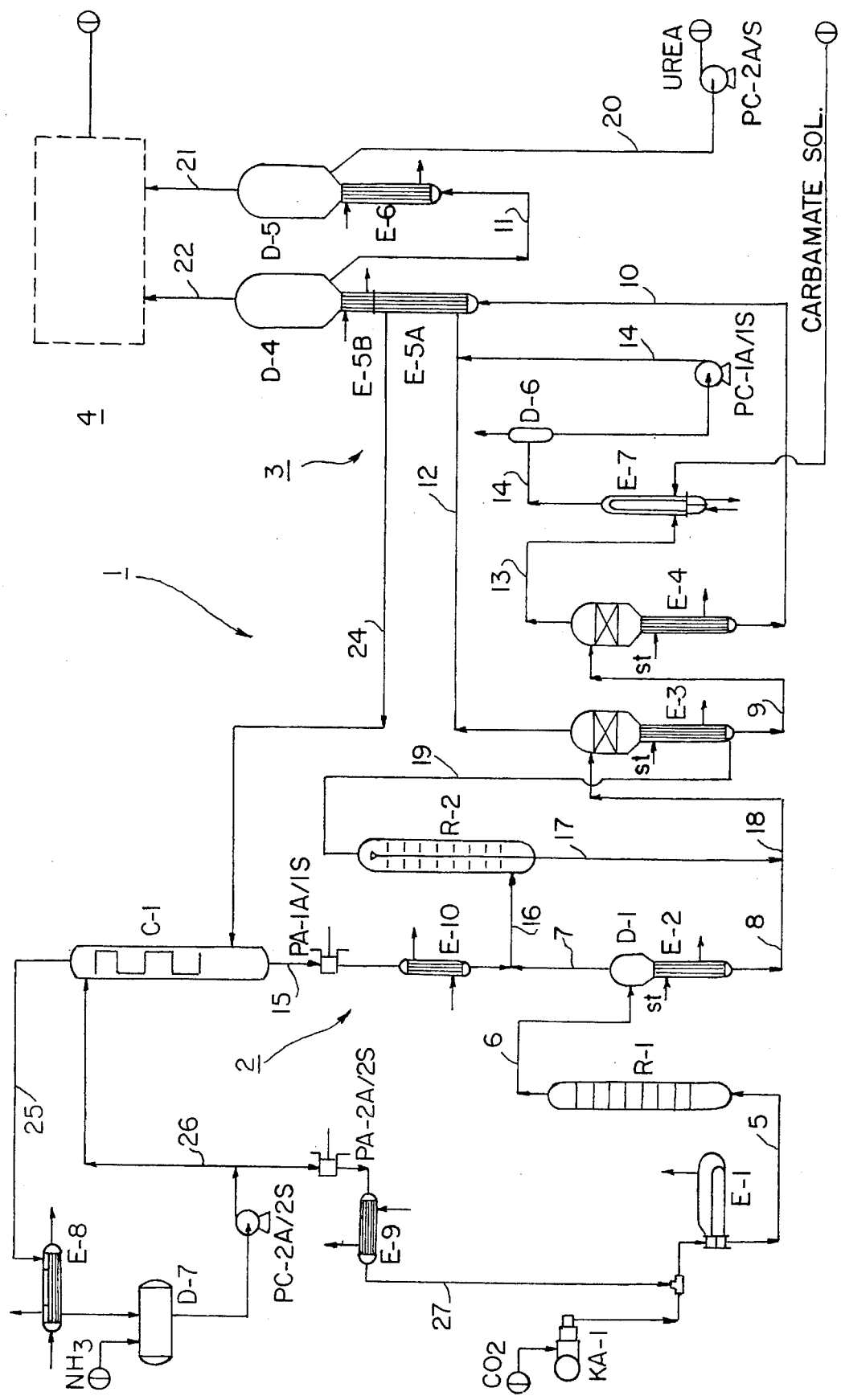

PLANT FOR THE PRODUCTION OF UREA IN REACTION SPACES WITH DIFFERENT YIELDS

This is a Continuation of application Ser. No. 08/236,574, filed on May 2, 1994 now U.S. Pat. No. 5,523,482.

BACKGROUND OF THE INVENTION

1. Field of the Invention

From a general point of view, the present invention refers to a process of producing urea.

More particularly, the invention refers to a process of producing urea of the type comprising the steps of:

reacting substantially pure ammonia and carbon dioxide in a first reaction space, so as to obtain a first reaction mixture including urea and carbamate;

subjecting the first reaction mixture to a thermal decomposition treatment of the carbamate so as to obtain a flow of ammonia and carbon dioxide and an independent flow of urea, undecomposed carbamate and free ammonia in aqueous solution;

feeding the ammonia and carbon dioxide flow to a second reaction space;

feeding the flow of urea and undecomposed carbamate in a urea recovery section so as to obtain independent flows of urea, ammonia and carbamate;

recycling the flow of carbamate so obtained in the second reaction space;

reacting ammonia and carbon dioxide obtained from the thermal decomposition treatment and the recycled carbamate in the second reaction space, so as to obtain a second reaction mixture.

The invention also refers to a plant for carrying out the above mentioned process.

2. Description of the Related Art

As is known, in urea production, the need is more and more felt of having on the one hand plants with higher capacity and operational flexibility and, on the other hand, lower investment and operating costs, especially in energetic terms.

To this aim, various urea production processes have been proposed and reduced to practice in the art which are substantially based on conversion reactions carried out with different yields in reactors disposed in parallel one to the other, as described, for example, in European Patent Application EP-A-0 479 103.

More particularly, such processes propose to carry out a first reaction in a primary high-yield reactor fed by substantially pure carbon dioxide and ammonia and optionally by highly pure recovered ammonia, as well as a second reaction in an auxiliary lower yield reactor, in parallel to the preceding one, fed by a solution (substantially comprising unreacted carbamate) coming from a urea recovery section.

In a second known process, described for example in European Patent Application EP-A-0 544 056 by the same Applicant, the auxiliary lower yield reactor is fed not only by the solution coming from a urea recovery section, but also by ammonia and carbon dioxide obtained from a thermal decomposition treatment of the reaction mixture leaving the high-yield reactor.

Even if these processes and in particular the last one substantially attain to the aforementioned aim, they may be affected in operation by a certain inelasticity.

The operating conditions of the auxiliary reactor, in particular temperature and ammonia/carbon dioxide molar ratio, are in fact exclusively controlled by regulating the temperature of the thermal decomposition treatment of the reaction mixture leaving the primary reactor, with the result that to maintain the desired temperature in the auxiliary reactor, the ammonia/carbon dioxide molar ratio can shift from the optimal value and vice-versa.

The plant which carries out the above mentioned process is affected by a number of different structural constraints that make its manufacture more complex and expensive.

In order to ensure a correct feeding to the auxiliary reactor of the vapors obtained from the thermal decomposition of the reaction mixture leaving the high-yield reactor, in fact, the plant must be provided with specific structures which permit to position the auxiliary reactor at a higher level with respect to the equipments in which the thermal decomposition treatment takes place.

SUMMARY OF THE INVENTION

The technical problem underlying the present invention is that of providing a process of producing urea that will allow to overcome the drawbacks referred to in the cited prior art.

This problem is solved, according to the invention, by a process as indicated hereinabove, which is characterized in that the ammonia/carbon dioxide molar ratio and the reaction temperature in said second reaction space, are independently controlled by respectively regulating the temperature of said thermal decomposition treatment and the temperature of said recycled carbamate flow.

Advantageously, the reaction in the first reaction space between substantially pure ammonia and carbon dioxide is carried out with partial heat removal at a pressure between 210 and 280 bar, at a temperature not higher than 210° C. and with an ammonia/carbon dioxide molar ratio not higher than 4.

Preferably, the above cited reaction is carried out in two consecutive steps by feeding pure ammonia and carbon dioxide to a condenser-prereactor so as to obtain a solution comprising urea and carbamate, which is sent to a high-yield reactor of the so-called "once through" type.

In accordance with an aspect of the invention, the heat removal takes place during a pre-reaction between ammonia and carbon dioxide, and allows an advantageous production of medium-pressure steam (9–10 bar), which may be used to carry out other steps of the process.

Advantageously, it is also possible to operate with an ammonia/carbon dioxide molar ratio lower than 4, and preferably equal to about 3.6, with an advantageous volume reduction of the high-yield reactor and a reduction of the energy required for pre-heating the reagents to the reaction temperature.

To this aim and in accordance with another aspect of the present invention, it should be noted that the thermal control of the reaction between ammonia and carbon dioxide in the first reaction space is advantageously carried out by simply controlling the temperature of the ammonia feed at values of from 40° to 150° C.

According to the invention, the thermal decomposition treatment of the carbamate present in the reaction mixture leaving the first reaction space, is carried out at a pressure of from 140 to 160 bar and at a temperature of from 180° to 210° C.

In accordance with another advantageous feature of the invention, the above mentioned decomposition step may be carried out more easily and at lower temperatures with respect to the prior art processes, thanks to the reduced water quantity—limited to the reaction water only—of the flow which undergoes to the thermal treatment.

Advantageously, moreover, the working pressure in this step is selected among the above cited range in such a way as to overcome the working pressure in the second reaction space, thus allowing an easy entrance in the latter space of the gaseous phase produced by decomposing the carbamate (substantially a mixture of ammonia and carbon dioxide).

In accordance with another feature of the present invention, the temperature of the thermal decomposition treatment of the carbamate, is selected in the above mentioned interval at a value which allows to control the ammonia/carbon dioxide molar ratio at the optimal value in order to carry out the following process step in the second reaction space.

The ammonia and carbon dioxide obtained from the above mentioned thermal decomposition treatment of the carbamate are fed to the second reaction space, where they react with the recycled carbamate leaving in solution form the recovery and purification steps of the urea produced.

According to the invention, these steps provide the separation by evaporation of unreacted ammonia, carbon dioxide and water formed during the reaction from the urea produced, as well as the subsequent separation by distillation of the ammonia from a carbamate solution obtained from carbon dioxide and water.

Preferably, this distillation step takes place at a pressure of from 16 to 20 bar, operating at a temperature of from 70° to 120° C.

According to the invention, the ammonia so obtained is recycled to the first reaction space as well, upon mixing with pure ammonia, fed from the outside, and heating to the desired temperature.

Preferably, the above mentioned reaction in the second reaction space is carried out at a pressure of from 140 to 150 bar, and at a temperature of from 180° to 200° C., and operating with an ammonia/carbon dioxide molar ratio of from 4.0 to 4.8.

Advantageously, the reaction temperature is maintained within the above mentioned range by simply controlling the temperature of the carbamate solution recycled from the urea recovery section. Preferably, the temperature of the carbamate solution is set at a value of from 70° to 150° C.

BRIEF DESCRIPTION OF THE DRAWINGS

Other features and advantages of the present invention will be better apparent from the description of an embodiment of the process according to the invention, given hereinbelow, by way of illustration but not of limitation, with reference to the plant illustrated in the attached drawing.

DETAILED DESCRIPTION OF THE PREFERRED EMBODIMENTS

In this drawing, with 1 is generally indicated a urea production plant comprising a synthesis section 2, a urea recovery section 3 operating at medium pressure, and a section 4 operating under vacuum in order to recover ammonia.

Section 2 comprises, arranged in series, a first reactor R-1 for urea synthesis, an apparatus E-2 for the thermal decomposition of carbamate and a second urea synthesis reactor R-2.

According to the invention, carbon dioxide and fresh ammonia are pre-mixed together and are fed tube side, by means of a compressor KA-1 and a pump PA-2A/2S respectively, to a condenser/pre-reactor E-1 connected to the reactor R-1 by means of a conduit 5.

Advantageously, part of the reaction heat developed in E-1 is removed by a suitable cooling fluid, which flows shell-side.

Preferably, this fluid is water, which is transformed into medium-pressure steam by the heat developed in E-1 at high thermal level (approximately 170° C.) and sent, in a conventional way which is not shown, to other apparatuses of the plant 1.

The reactor R-1, is in turn connected—by means of a conduit 6—to the above mentioned apparatus E-2 for the thermal decomposition of the carbamate, which is preferably of the film type and is provided with a separator D-1.

The apparatus E-2 is in fluid communication with reactor R-2 and with the recovery section 3 respectively, by means of conduits 7 and 8.

Reference numbers 17, 18 and 19 indicate respective conduits for feeding an urea solution and a vapor phase including unreacted ammonia and carbon dioxide from the reactor R-2 to a first medium-pressure evaporator E-3, which is part of the recovery section 3 of the urea produced.

This same recovery section comprises in turn medium-pressure evaporators E-4, E-7, as well as evaporators E-5, E-8 connected in series to one another by means of conduits indicated with reference numbers 9 to 14.

Reference numbers 20, 21 and 22 indicate conduits for respectively feeding the produced urea to conventional finishing apparatuses, which are not shown, and ammonia-containing vapors to the vacuum section 4.

According to a characteristic of the invention, the vapors leaving the evaporators E-3, E-4 and E-7, which contain ammonia, carbon dioxide and reaction water, are condensed shell-side in evaporator E-5 and are sent—by means of conduit 24—to a distillation column C-1.

The latter is connected in turn to a condenser E-8 of the ammonia vapors leaving the top of column C-1, by means of a conduit 25, and to the auxiliary reactor R-2, by means of conduits 15 and 16, respectively.

The ammonia condensed in E-8 is collected in a conventional tank D-7, from which it is withdrawn by pump PC-2A/2S after being mixed with fresh ammonia.

This pump is in fluid communication, by means of conduits 26 and 27, with the head of the column C-1 and with the condenser/pre-reactor E-1, respectively.

In accordance with a characteristic of this invention, on the conduit 27 and downstream of the pump PA-2A/2S, means are provided, such as, for example, a shell-and-tube heat exchanger E-9, for maintaining within optimal values the temperature of the ammonia fed to the condenser/prereactor E-1.

With reference to the plant described above, an example of the process according to the invention is given hereinbelow, by way of illustration but not of limitation.

EXAMPLE 1

In accordance with the invention, a daily production of 500 metric tons of urea was obtained from the plant described above.

The heat developed by the reaction:

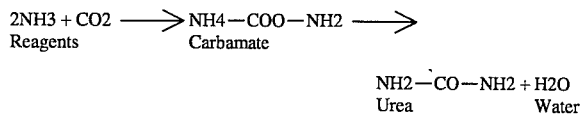

$$NH_2-CO-NH_2 + H_2O$$
Urea    Water was partially removed in the condenser/pre-reactor E-1 and used to generate medium-pressure steam (9 bar), used in various equipments of plant 1.

The synthesis reaction in the first reaction space took place in the following conditions:

| | |
|---|---|
| $NH_3/CO_2$ | 3.6 mol |
| $H_2O/CO_2$ | 0.0 mol |
| $NH_3$ inlet temperature | 100° C. |
| $CO_2$ inlet temperature | 150° C. |
| Reaction temperature | 195° C. |
| Pressure | 240 bar |
| $CO_2$ conversion yield | 75.0% |
| Reactor lining | AISI 316 L.U.G. |

The urea solution leaving reactor R-1 was subjected to flash from 240 to 155 bar in the separator D-1 and then to a thermal decomposition treatment in the tube bundle of E-2 at a temperature of approximately 190° C.

The vapors produced in E-2 were sent to R-2 by means of conduit 7, whereas the urea solution was mixed with the solution leaving the reactor R-2 and fed by means of conduit 18 to the medium pressure decomposer E-3.

The auxiliary reactor R-2 was fed with vapors leaving E-2 and with a carbamate solution coming from the distillation column C-1 and recycled by means of the pump PA-1A-/1S and the conduits 15 and 16.

In accordance with a characteristic of this invention, the working temperature in the secondary reactor R-2 was constantly maintained within optimal values by heating the recycled carbamate solution by means of the heat exchanger E-10, while the ammonia/carbon dioxide molar ratio was regulated supplying the most appropriate heat amount to the thermal decomposition apparatus E-2.

The operating conditions of the secondary reactor R-2 were the following:

| | |
|---|---|
| $NH_3/CO_2$ | 4.5 mol |
| $H_2O/CO_2$ | 1.3 mol |
| $CO_2$ conversion yield (%) | 60.0% |
| Pressure | 150 bar |
| Temperature | 190° C. |

Then, the vapors leaving from top of the auxiliary reactor R-2 were also sent to evaporator E-3 in the urea recovery section 3 from which a gaseous phase including carbon dioxide and ammonia vapors, sent shell-side to the vacuum evaporator E-5, and a urea solution, sent to evaporator E-4, were obtained.

In the latter, another proportion of carbon dioxide and ammonia vapors was obtained, which was also sent, after condensation in E-7, to evaporator E-5 by means of pump PC 1A/1S.

The above mentioned gaseous phase, including carbon dioxide and ammonia vapors, was then subjected, after condensation in conventional apparatuses which are not shown, to distillation in column C-1, so as to obtain substantially pure ammonia recycled to E-1 and the above mentioned carbamate solution recycled to the auxiliary reactor R-2.

From evaporators E-5 and E-8 a urea solution, which was sent to subsequent treatments, and ammonia vapors treated in section 4, were obtained.

Altogether, 75% of the urea production was obtained in R-1, while the remaining 25% was obtained in R-2, with a weighed average efficiency of the two reactors close to 71.5%.

Consumptions:

The specific consumptions, referred to 1000 kg of urea produced, were the following:

| | |
|---|---|
| liquid $NH_3$ at 32° C., 18 bar (kg) | 568 |
| $CO_2$ (kg) | 734 |
| Steam at 25 bar (kg) | 400 (*) |
| Electric energy (kWh) | 115 |

*water treatment excluded.

The numerous advantages of this invention are immediately evident from what is described and illustrated above.

Firstly, a high urea yield can be obtained in the synthesis section 2 with simple and inexpensive recovery sections downstream thereof.

Secondly, the temperature and ammonia/carbon dioxide molar ratio in the auxiliary reactor R-2 can be maintained within optimal values in a swift and efficient way by respectively regulating the temperature of the carbamate solution recycled to R-2 and the temperature of the thermal decomposition treatment of the urea solution leaving reactor R-1.

Moreover, the two-steps urea synthesis reaction carried out in the first reaction space results in an advantageous decrease of the ammonia/carbon dioxide molar ratio in the main reactor R-1, with a reduction of the required volumes and a lower heat consumption for preheating the reagents and maintaining the working temperature.

Last but not least advantage is the use of a condenser/pre-reactor E-1 in the first reaction space, which allows an advantageous production of medium-pressure steam, as well as the possibility of directly heating the urea solution sent to evaporator E-3 (process-to-process heat exchange).

I claim:

1. A plant for producing urea comprising:

(A) a first urea synthesis reactor (R-1);

(B) a second urea synthesis reactor (R-2);

(C) a recovery section (3) of urea, ammonia and carbamate, respectively;

(D) an apparatus (E-2) for thermal decomposition of carbamate connected to said first urea synthesis reactor (R-1), to said second urea synthesis reactor (R-2), and to said recovery section (3) of urea, ammonia and carbamate, respectively;

(E) at least one conduit (15, 16) for recycling the carbamate obtained in said recovery section (3) to said second urea synthesis reactor (R-2); and (F) a means (E-10) on said at least one conduit (15, 16) for regulating the temperature of the carbamate recycled to the second urea synthesis reactor (R-2).

2. A plant according to claim 1, wherein said means (E-10) to regulate the temperature of the recycled carbamate comprise a shell-and-tube heat exchanger.

3. A plant according to claim 1, wherein said first reactor (R-1) is of the type with partial heat removal.

4. A plant according to claim 1, wherein it also comprises a condenser/pre-reactor (E-1) upstream of said first reactor (R-1).

5. A plant according to claim 1, wherein said first reactor (R-1) is a so-called "once through" high-yield reactor.

* * * * *